United States Patent [19]
Cloyd et al.

[11] 4,192,887
[45] Mar. 11, 1980

[54] RUMINANT COCCIDIOSTATS

[75] Inventors: Grover D. Cloyd; Robert L. Miller; Donald M. Lucas, all of Richmond, Va.

[73] Assignee: A. H. Robins Company, Incorporated, Richmond, Va.

[21] Appl. No.: 913,767

[22] Filed: Jun. 8, 1978

[51] Int. Cl.² .............................................. A61K 31/35
[52] U.S. Cl. .................................................... 424/283
[58] Field of Search ......................................... 424/283

[56] References Cited

U.S. PATENT DOCUMENTS

| | | | |
|---|---|---|---|
| 3,857,948 | 12/1974 | Tanaka et al. | 424/283 |
| 4,035,481 | 7/1977 | Berg et al. | 424/283 |
| 4,085,224 | 4/1978 | Berg et al. | 424/283 |

OTHER PUBLICATIONS

Hoechst–Chem. Abst., vol. 88 (1978), p. 36265w.

*Primary Examiner*—Sam Rosen

[57] ABSTRACT

Methods of preventing and controlling coccidiosis in ruminant animals and for improving rate of weight gain by oral administration of salinomycin or 4-methylsalinomycin are disclosed.

4 Claims, No Drawings

RUMINANT COCCIDIOSTATS

BACKGROUND OF THE INVENTION

1. Field of Invention

This invention is concerned with methods of controlling and combatting coccidiosis and improving rate of weight gain in ruminant animals, having been exposed to or infected with coccidia parasites, by oral administration of certain salinomycins, namely salinomycin and its 4-methyl derivative and their acceptable salts and $C_2$–$C_6$ esters and salts thereof.

Uncontrolled development of the coccidia parasite in ruminant animals can debilitate the animal and aggravate other diseases present. Infection with coccidia in one animal can readily be spread throughout the entire group such as sheep and cattle in the feed lot through excretion of coccidia oocysts and subsequent ingestion by uninfected ruminants. The salinomycins interfere in the life cycle of coccidia in ruminants, reducing oocyst production and the spread of coccidiosis.

2. Description of the Prior Art

Use of salinomycin as an anticoccidial agent in chickens is disclosed in U.S. Pat. No. 3,857,948 and use of salinomycin in a method of increasing feed-utilization efficiency in a ruminant animal by increasing the proportion of propionate in the rumen has been disclosed in U.S. Pat. No. 4,085,224. Use of 4-methylsalinomycin to increase the proportion of propionate has also been disclosed in U.S. Pat. No. 4,009,262. The present invention is based on the finding that the salinomycins pass from the rumen into the gut and interfere in the life cycle of the coccidia parasite.

Medication such as decoquinate which is 6-decyloxy-7-ethoxy-4-hydroxy-3-quinoline carboxylic acid ethyl ester and amprolium have been used in prevention of bovine coccidiosis as described in the March, 1977 issue of the publication *Animal Nutrition and Health*, p. 6.

SUMMARY OF THE INVENTION

The present invention provides novel methods of controlling and combatting coccidiosis in ruminant animals such as lambs, calves and feed-lot heifers and steers and improving rate of gain and consists of administering orally to a ruminant animal an amount of salinomycin or its 4-methyl derivatives effective in substantially preventing development and growth of coccidia on the gut of the animal. Not only is infection of the individual animal reduced or eliminated but the spread of the disease to other members of the herd or group is prevented. As a result of the control of coccidia parasites, weight gain per day is increased.

It is therefore an object of the present invention to provide a method of controlling and eliminating the development of the coccidia parasite in the gut of ruminant animals by oral administration of salinomycin or 4-methyl salinomycin.

Another object is to prevent the spread of coccidiosis in ruminant animals wherein by oral administration of salinomycin or 4-methyl salinomycin to a ruminant animal, the life cycle of the coccidia parasite is interrupted and the numbers of coccidia oocysts which spread the disease are greatly reduced.

Another object is to provide a means to improve rate of growth or weight gain per day by the reduction and/or elimination of coccidia parasites in ruminants.

These and other objects of the present invention will become apparent to one skilled in the art from a consideration of the following detailed embodiments.

DETAILED DESCRIPTION OF THE INVENTION

The salinomycins useful as anticoccidium agents in the ruminant gut are the free acids of salinomycin, and 4-methyl salinomycin and salts, $C_2$–$C_6$ esters thereof which may be prepared from anhydrides according to procedures of U.S. Pat. No. 4,035,481. By salts is meant those salts which on neutralization with acid yield the free salinomycins, and by esters is meant those which effectively yield the salinomycins of this invention on hydrolysis.

Salinomycin used in the method of the present invention may be prepared by culturing *Streptomyces albus* under conditions disclosed in U.S. Pat. No. 3,857,948, said disclosure being hereby incorporated as part of this application and wherein the structure of salinomycin is also disclosed. The preparation of 4-methylsalinomycin is described in U.S. Pat. No. 4,009,262. Any non-toxic salt or other pharmaceutically acceptable form of salinomycin and 4-methylsalinomycin or any non-toxic composition or diluent containing these salinomycins is suitable for purposes of this invention.

Preparation of Crude Salinomycin Mycellial Cake

An inoculum was prepared by growing the salinomycin-producing organism *Streptomyces albus—ATCC 21,838* on agar slants made up of 10 g. soluble starch, 2 g. yeast extract, 12 g. agar and sufficient water to make 1 liter. Prior to inoculation the solution was adjusted to pH 7 and autoclaved at 120° C. for 20 minutes. After 1 loopful of cells was inoculated on the agar slant, the tube was plugged with cotton and incubated at 30° C. for 5–7 days. After sufficient growth occurred the cotton plug was replaced with a rubber stopper and the culture stocked in a refrigerator at 5° C. The stock culture must be used within 6 months. A sterilized seed medium (80 ml) having in wt/vol % 4.0 glucose, 1.0 soybean flour, 1.0 dried brewers' yeast and 0.2 $CaCO_3$ (pH 6.5–7.0) was inoculated with 0.5 ml. of the stock culture in a 500 ml flask and shaken for 48 hr. at 33° C. The seed culture was scaled up to 16 liter volume in a 30-liter stainless steel laboratory fermenter by adding 160 ml of the stock culture to sterilized solutions and mixtures of 640 g. glucose, 160 g. soybean flour, 160 g. dried Brewer's yeast, 32 g. $CaCO_3$ and 32 g. silicone antifoamer (KM68-2F, Shin-Etsu Chemical Co., Ltd. in Japan). For this the glucose and other materials were sterilized separately at 120° C. for 20 minutes with saturated steam and mixed after cooling to 33° C. The culture was maintained at 33° C. for 48 hours after inoculation. Agitation at the rate of 350 r.p.m. and aeration at the rate of 16 L/min under inner pressure of 0.3–1.0 $Kg/cm^2$ were carried out throughout the culture. Production fermentation was started using four liters of the culture to inoculate the sterilized production medium composed of:

| Glucose | 2.0 kg | KCl | 0.4 kg |
|---|---|---|---|
| Soybean oil | 40 liters | $CaCO_3$ | 2.0 kg |
| Soybean flour | 2.0 kg | $K_2HPO_4$ | 40.0 g |
| Defatted wheat embryo | 2.0 kg | $MgSO_4 \cdot 7H_2O$ | 40.0 g |
| $(NH_4)_2SO_4$ | 1.2 kg | Silicone Antifoamer | 400.0 g |

-continued

NaCl    0.4 kg    (KM68-2F Shin-Etsu Chemical Co.)

The pH of the production medium was adjusted to pH 7.5 with aqueous sulfuric acid before inoculation. Total volume of the production fermentation was 400 liters. The fermentation was conducted in 600-liter stainless steel vessel at 33° C. for 210 hours with an agitator moving at the rate of 250 r.p.m. and aeration at the rate of 400 liters/min. under inner pressure of 0.3–1.0 kg/cm$^2$. The broth was extracted once with ethyl acetate and the extract sprayed on silica sand and lyophylized. The dried product contained 27.2 wt% salinomycin sodium.

Assay for Salinomycin

The microbiological assay for salinomycin content and potency employs the standard cylinder plate method as described for penicillin in Code of Federal Regulations 141a.1, using in this instance *Bacillus subtilis* as the test microorganism and an agar medium at pH 5.8. Salinomycin is washed from the cake prior to assay and the methanolic solution diluted to about 18% salinomycin. Unextractable salinomycin is determined by adding salinomycin of known assay to a similar substrate and correction made on the unknown for the amount retained by the cake.

The salinomycins of this invention may be administered in the feed of ruminants, particularly feed-lot ruminants such as heifers, steers and lambs, or mild-fed ruminants such as calves and lambs, to control coccidia parasites generally in amounts of 5 to 45 g/ton of feed, preferably about 15 to 45 g/ton. The salinomycins may also be administered in unit dosage form in the form of capsules, tablets, slurries, etc. for the control of coccidiosis, generally in amount of 0.5 to 2.0 mg/kg body weight of the ruminant.

When it is desirable to therapeutically treat ruminants for coccidia infestation for short periods of time, i.e., a few days, higher concentrations of the salinomycins in the feed may be desirable up to 90 mg or more/kg of feed.

EXAMPLE 1

(Salinomycin-Feedlot Lambs)

Two groups of 10 lambs each were fed in two separate dry lots on a diet containing varying amounts of salinomycin sodium of 5 to 45 g/ton of feed over an 80-day fattening period. On days 43 and 80 of the fattening period, fecal samples were obtained for each lamb and the fecal samples were scored as to the relative concentration of coccidial oocysts present.

The relative oocyst concentration in lamb fecal samples was determined by the fecal flatation method and scored as follows:
0 = no oocysts
+ = few oocysts
+ + = numerous oocysts
+ + + = oocysts thick
+ + + + = large number of oocyst Oocyst scores for 43 and 80 days on individual lambs are in Tables 1 and 2 and the composite result is in Table 3. Composition of the ration as fed as a weight percent of composition was 30 grass hay, 59 corn grain, 10 soybean meal and 1.0 limestone. Vitamin A palmitate to supply 1100 IU vitamin A per kg of ration was mixed in the feed. Crude protein value of the feed was 10.7% and TDN was 62.7%. Salinomycin sodium was added to the ration at levels of 0 (control), 5, 15, 30 and 45 g/ton.

Oocyst scores for control lambs in Example 1 indicate coccidia were present in most of the control lambs at days 43 and 80 of feeding in the dry lot. Addition of 5 g salinomycin sodium per ton of feed gave a slight improvement in oocyst scores, and addition of 15, 30 and 45 g/ton resulted in considerable reduction in the number of lambs exhibiting coccidial infestation by the presence of oocysts in the feces. The few lambs on 15–45 g/ton treatment which had oocysts present in the feces had relatively few oocysts as compared to the greater number present in controls.

TABLE I

EXAMPLE 1
OOCYSTS SCORES - DAY 43 SHEEP FECAL SAMPLES

| REP | CONTROL LAMB # | SCORE | 5 g SALINOMYCIN/ton LAMB # | SCORE | 15 g SALINOMYCIN/ton LAMB # | SCORE | 30 g SALINOMYCIN/ton LAMB # | SCORE | 45 g SALINOMYCIN/ton LAMB # | SCORE |
|---|---|---|---|---|---|---|---|---|---|---|
| I | 901 |  | 781 | ++ | 804 | 0 | 799 | 0 | 604 |  |
|  | 916 | 0 | 809 | 0 | 815 | 0 | 893 | 0 | 605 | 0 |
|  | 920 | ++ | 906 | + | 913 | 0 | 931 | 0 | 837 | 0 |
|  | 926 | + | 908 |  | 918 | 0 | 954 | 0 | 907 |  |
|  | 927 | ++ | 911 | 0 | 924 | 0 | 963 | 0 | 910 | 0 |
|  | 935 | ++ | 934 | ++ | 939 | 0 | 964 | 0 | 957 | 0 |
|  | 940 | ++++ | 941 |  | 952 |  | 974 | 0 | 960 |  |
|  | 957 | 0 | 982 |  | 981 | 0 | 975 | 0 | 978 | + |
|  | 983 | +++ | 996 | 0 | 985 | 0 | 989 | 0 | 987 | 0 |
|  | 990 | 0 | 999 |  | 998 |  | 997 | 0 | 988 | + |
| II | 802 | + | 607 | + | 602 | 0 | 865 | 0 | 603 |  |
|  | 902 | ++ | 873 | + | 825 |  | 912 | 0 | 610 | + |
|  | 921 | 0 | 909 | + | 888 | 0 | 919 |  | 903 | + |
|  | 923 |  | 925 | 0 | 917 | 0 | 930 |  | 932 | 0 |
|  | 933 | + | 945 | 0 | 928 | 0 | 937 | 0 | 958 | 0 |
|  | 936 | + | 959 | + | 929 | 0 | 947 | 0 | 965 | 0 |
|  | 943 |  | 962 | ++ | 948 | 0 | 968 | 0 | 971 |  |
|  | 956 | +++ | 976 | ++ | 949 | 0 | 972 | + | 979 | 0 |
|  | 969 |  | 986 | 0 | 950 |  | 991 | 0 | 980 | 0 |
|  | 970 | + | 993 | + | 966 | 0 | NT |  | 984 |  |

TABLE 2

EXAMPLE 1
OOCYSTS SCORES - DAY 80 SHEEP FECAL SAMPLES

| REP | CONTROL LAMB # | SCORE | 5 g SALINOMYCIN/ton LAMB # | SCORE | 15 g SALINOMYCIN/ton LAMB # | SCORE | 30 g SALINOMYCIN/ton LAMB # | SCORE | 45 g SALINOMYCIN/ton LAMB # | SCORE |
| --- | --- | --- | --- | --- | --- | --- | --- | --- | --- | --- |
| 1 | 901 | +++ | 781 | 0 | 804 | 0 | 799 | 0 | 604 | 0 |
|   | 916 | ++++ | 809 | ++ | 815 | 0 | 893 | 0 | 605 | 0 |
|   | 920 | 0 | 906 | +++ | 913 | 0 | 931 |   | 837 | 0 |
|   | 926 | ++ | 908 | 0 | 918 | 0 | 954 | 0 | 907 | 0 |
|   | 927 | ++++ | 911 | 0 | 924 | 0 | 963 | 0 | 910 | 0 |
|   | 935 | +++ | 934 | +++ | 939 | + | 964 |   | 957 | + |
|   | 940 | ++ | 941 |   | 952 | 0 | 974 | 0 | 960 | 0 |
|   | 957 | + | 982 | 0 | 981 | 0 | 975 |   | 978 | 0 |
|   | 983 | +++ | 996 | 0 | 985 | 0 | 989 | 0 | 987 | 0 |
|   | 990 | 0 | 999 | 0 | 998 | 0 | 997 | 0 | 988 | 0 |
| 11 | 802 | +++ | 607 |   | 602 | + | 865 | 0 | 603 |   |
|   | 902 | + | 873 | + | 825 | 0 | 912 | 0 | 610 | 0 |
|   | 921 | ++ | 909 | 0 | 888 | 0 | 919 | 0 | 903 | 0 |
|   | 923 | ++ | 925 |   | 917 | 0 | 930 | 0 | 932 |   |
|   | 933 | + | 945 | 0 | 928 | 0 | 937 | 0 | 958 | 0 |
|   | 936 | 0 | 959 | ++ | 929 |   | 947 | 0 | 965 | 0 |
|   | 943 | ++ | 962 | +++ | 948 | 0 | 968 | 0 | 971 | 0 |
|   | 956 | ++++ | 976 | +++ | 949 | 0 | 972 | 0 | 979 | 0 |
|   | 969 |   | 986 | 0 | 950 | 0 | 991 | 0 | 980 | 0 |
|   | 970 | ++ | 993 | 0 | 966 | 0 | NT | 0 | 984 | 0 |

TABLE 3

EXAMPLE 1
SUMMARY OF OOCYST SCORES FOR FATTENING LAMBS FED DIFFERENT LEVELS OF SALINOMYCIN

| LEVEL OF SALINOMYCIN IN FEED (g/ton) | SAMPLING TIME (day) | SCORES[a] NO OOCYSTS | FEW OOCYSTS | NUMEROUS OOCYSTS | OOCYSTS THICK | LARGE NO. OF OOCYSTS | TOTAL SAMPLES/ TREATMENT |
| --- | --- | --- | --- | --- | --- | --- | --- |
| 0 | 43 | 4 | 5 | 4 | 2 | 1 | 16 |
|   | 80 | 3 | 3 | 6 | 4 | 3 | 19 |
| 5 | 43 | 6 | 6 | 4 | 0 | 0 | 16 |
|   | 80 | 10 | 1 | 2 | 4 | 0 | 17 |
| 15 | 43 | 16 | 0 | 0 | 0 | 0 | 16 |
|   | 80 | 17 | 2 | 0 | 0 | 0 | 19 |
| 30 | 43 | 16 | 1 | 0 | 0 | 0 | 17 |
|   | 80 | 17 | 0 | 0 | 0 | 0 | 17 |
| 45 | 43 | 10 | 4 | 0 | 0 | 0 | 14 |
|   | 80 | 17 | 1 | 0 | 0 | 0 | 18 |

[a]Values in the table represent the number of samples on each treatment which received that oocyst score.

EXAMPLE 2

(Salinomycin—Calves, 0-1 mg/kg)

Three week old calves housed in individual pens and fed a milk replacer diet (twice daily) were administered orally gelatin capsules containing varied amounts of salinomycin as mycellial cake as hereinafter described at 0 (controls), 0.33, 0.66 and 1.0 mg/kg body weight twice daily. On the second day after initiation of the salinomycin, all calves were inoculated (drenched) with 100,000 sporulated E. bovis oocysts. Fecal samples were obtained from each calf twice daily, starting 14 days post inoculation, for determination of the coccidial oocyst concentration. The peak oocyst concentrations in the feces of calves on each treatment are expressed as the geometric mean in Table 4.

Fecal oocyst concentration was substantially reduced by levels of 0.66 and 1.0 mg. salinomycin/kg body weight/day and at these dosage levels of salinomycin, the presence of clinical signs of coccidiosis (bloody diarrhea, tissue sloughing, etc.) among the calves was substantially reduced, whereas in the control group (no salinomycin) symptoms of severe clinical coccidiosis were observed with 50% deaths by 25 days post inoculation with coccidia oocysts. No deaths occurred in any of the groups treated with salinomycin.

Table 4

Effect of Salinomycin on Peak Oocyst Passage by Calves (Example 2)

| Salinomycin Dose, mg/kg/Day[a] | Number of Animals Tested | Peak Oocyst Counts[b] (Oocysts/g of Feces) |
| --- | --- | --- |
| 0.0 | 4 | 43,772 |
| 0.33 | 5 | 51,454 |
| 0.66 | 4 | 27,995 |
| 1.00 | 5 | 14,602 |

[a]By gelatine capsule, ½ of dose twice daily.
[b]Geometric mean for peak oocyst passage usually occurring 18-21 days after infection.

EXAMPLE 3

(Salinomycin—Calves, 0-2.0 mg/kg)

The procedure of Example 2 was followed except oral dosage levels of 0, 0.5, 1.0 and 2.0 mg/kg body weight per day were used. Results are in Table 5.

Table 5
Effect of 0–2 mg/kg Salinomycin on Peak Oocyst Passage by Calves (Example 3)

| Salinomycin Dose, mg/kg/Day[a] | Number of Animals Tested | Peak Oocyst Counts[b] (Oocysts/g of Feces) |
|---|---|---|
| 0 | 4 | 71,650 |
| 0.5 | 4 | 4,779 |
| 1.0 | 4 | 1,420 |
| 2.0 | 3 | 12 |

[a]By capsule ½ of dose twice daily.
[b]Geometric mean for peak oocyst passage usually occurring 18–21 days after infection.

Fecal oocyst concentration was substantially reduced at all levels of salinomycin dosage with essentially no oocyst passed at the 2.0 mg/kg level. The salinomycin substantially eliminated clinical symptoms of coccidiosis. Weight gain for the time period of the test is increased by about 8–20% for calves receiving salinomycin.

EXAMPLE 4

(4-Methylsalinomycin—Calves, 0–2 mg/kg)

When in the procedure of Example 3, 4-methylsalinomycin is substituted for salinomycin, a similar reduction in oocyst count is observed as well as elimination of clinical symptoms of the disease coccidiosis at 0.5–2.0 mg/kg body weight. Feed efficiency is increased by 10–15% and weight gain for the time period is increased by 8–20 percent.

EXAMPLE 5

(Salinomycin—Feed-lot Cattle)

A feed lot was divided in two and one half of a group of cattle averaging 700 lbs. each at the start were placed in each half. One half of the cattle are fed on a diet of corn silage and feed supplement over a period of 120 days. Composition of the feed on a tonnage basis is as follows:

| Feed Supplement[1] | |
|---|---|
| Soybean meal | 443 lb. |
| Dehydrated alfalfa | 95 lb. |
| Cane molasses | 95 lb. |
| Steamed bone meal | 35 lb. |
| Cobalt [premix[2]] | 12 lb. |
| Salinomycin, 30 grams[3] | |
| Vitamin A (Stabilized 6.8 million I.U.) | |
| Vitamin D 0.7 million I.U. | |
| Roughage | |
| Corn silage | 1,320 lb. |
| | 2,000 lb. |

[1]Furnishes supplemental nitrogen at the rate of 100% of the total dietary requirement.
[2]Contains cobalt carbonate at the rate of 1 oz. per 100 lb. of iodized salt.
[3]As crude salinomycin in mycellial cake described hereinabove.

The other half of the cattle are fed on the same diet but containing no salinomycin (controls). Collection of feces from both groups were made on day 60 from the beginning. Feces from the control group contained large numbers of coccidia oocysts whereas the group receiving the feed containing the salinomycin had few to no oocysts. A weight gain increase over the 120 day period averaging 10% was observed for the group fed the supplement containing the salinomycin compared to the group fed no salinomycin.

EXAMPLE 6

(4-Methyl Salinomycin—Feed Lot Cattle)

In accordance with the procedure of Example 5 but substituting in one half of the cattle, 4-methyl salinomycin for salinomycin, a weight gain increase over the 120 day period compared to the controls receiving no 4-methylsalinomycin of 9–12% is expectable and control of coccidiosis is obtained with 4-methylsalinomycin.

Various modifications and equivalents will be apparent to one skilled in the art and may be made in the compounds, compositions, and methods of the present invention without departing from the spirit or scope thereof, and it is therefore understood that the invention is to be limited only by the scope of the appended claims.

What is claimed is:

1. A method for combatting and controlling coccidiosis in ruminant animals which have been infected with coccidia parasites while at the same time improving the rate of weight gain per day of said animals which comprises orally administering to said animals in need thereof an effective amount of an agent selected from the group consisting of salinomycin, 4-methylsalinomycin, salts and esters thereof.

2. The method of claim 1 wherein said agent is administered in the feed of said ruminant animal in an amount in the range of 5 to 45 grams per ton of feed.

3. The method of claim 2 wherein salinomycin is administered to the ruminant animal.

4. The method of claim 2 wherein 4-methylsalinomycin is administered to the ruminant animal.

* * * * *